United States Patent
Marquez et al.

(10) Patent No.: US 10,555,689 B1
(45) Date of Patent: Feb. 11, 2020

(54) CPS PRESSURE BASED SENSING SYSTEM FOR SYMMETRY MEASUREMENTS

(71) Applicants: Juan Sebastian Marquez, Miami, FL (US); Ou Bai, Sunrise, FL (US); Roozbeh Atri, Miami, FL (US)

(72) Inventors: Juan Sebastian Marquez, Miami, FL (US); Ou Bai, Sunrise, FL (US); Roozbeh Atri, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 16/270,909

(22) Filed: Feb. 8, 2019

(51) Int. Cl.
*G01L 1/00* (2006.01)
*A61B 5/103* (2006.01)
*G01L 1/20* (2006.01)
*A61B 5/11* (2006.01)

(52) U.S. Cl.
CPC ............ *A61B 5/1038* (2013.01); *A61B 5/112* (2013.01); *G01L 1/205* (2013.01); *A61B 2562/0247* (2013.01)

(58) Field of Classification Search
CPC .................. A61B 5/1038; A61B 5/112; A61B 2562/0247; G01L 1/205

USPC ...................................................... 73/862.041
See application file for complete search history.

(56) References Cited

U.S. PATENT DOCUMENTS

| | | | |
|---|---|---|---|
| 7,540,342 B1 * | 6/2009 | Ein ......................... | A61H 3/04 180/19.1 |
| 2004/0173220 A1 * | 9/2004 | Harry ................... | A43B 3/0005 128/892 |
| 2011/0257928 A1 * | 10/2011 | Cunningham ........ | A61B 5/1116 702/150 |
| 2015/0305632 A1 * | 10/2015 | Najarian .............. | A61B 5/6831 600/301 |
| 2018/0049670 A1 * | 2/2018 | Markison ........... | A61B 5/02055 |

* cited by examiner

*Primary Examiner* — Max H Noori
(74) *Attorney, Agent, or Firm* — Saliwanchik, Lloyd & Eisenschenk (57) ABSTRACT

A cyber-physical system (CPS) pressure based sensing system and methods for assessing stance or mobility of a test subject standing or moving are provided. The CPS pressure based sensing system can include at least one piezoresistive transducer configured to obtain a plurality of measurements with respect to the stance or movements of the test subject, and a data analyzer configured to determine patterns of the stance or movement by performing machine learning classification on the plurality of measurements obtained by the at least one piezoresistive transducer.

20 Claims, 7 Drawing Sheets

CPS PRESSURE BASED SENSING SYSTEM FOR SYMMETRY MEASUREMENTS

GOVERNMENT SUPPORT

This invention was made with government support under CNS-1552163 awarded by National Science Foundation. The government has certain rights in the invention.

BACKGROUND

Gait asymmetry is characterized as the dynamic differences between contralateral limbs and is generally caused by disease, age, clinical interventions, or limb dominance. A number of mobile gait assessment systems have been developed for evaluation of gait asymmetry in persons with leg length discrepancy (LLD) or simulated leg length discrepancy (sLLD).

In the last few decades, gait analysis has been constrained to studies involving motion capture and the obligatory body markers and force mats. These constraints limit normal locomotion and remove important variation representative of each individual's gait. In addition to the behavioral constraints added by the non-mobile common gold standard measurement tools, high prices also deter medical professionals from making motion studies common practice.

More recent studies regarding gait analysis focus on using inertial measurement units (IMU) to assess asymmetry in gait, extracting gait features, or differentiating disease states. However, these designs have limited applications for LLD or sLLD, because LLD or sLLD leads to significant changes to gait in ground reaction forces (GRF). As a result, the representative kinetic components of GRF cannot be effectively measured by IMU sensors.

BRIEF SUMMARY

A major challenge for conventional gait analysis is the difficulty associated with pattern recognition, for which supervised learning techniques can be used to attempt to find a function representative of training sample pairs. The supervised learning techniques may be divided into memory-based learning techniques and non-memory-based learning techniques. However, both memory and non-memory-based techniques suffer from relying on a single hypothesis derived from the training space. This proves problematic when several suggested hypotheses provide the same accuracy based on training data, or when the supervised learning gets stuck on local minima due to computational constraints.

Several machine learning-based classifiers, such as decision trees, artificial neural networks, and genetic algorithms, have been investigated to differentiate disease states or to segment motion data by classifying gait phases. Nevertheless, in the case of low sLLD, because the events of data are closely related, separation may prove difficult, thereby significantly decreasing the predictive accuracy of these classification models.

Thus, there continues to be a need in the art for improved designs and techniques to accurately and reliably assess gait asymmetry in persons with leg length discrepancy (LLD) or simulated leg length discrepancy (sLLD).

Embodiments of the subject invention pertain to assessment of stance or mobility of a test subject standing or moving by using a cyber-physical system (CPS) pressure based sensing system.

In an embodiment, a CPS pressure based sensing system can comprise: a sensing and data acquisition device comprising at least one piezoresistive transducer; and a data analyzer communicating with the sensing and data acquisition device. The at least one piezoresistive transducer can be configured to obtain a plurality of measurements with respect to the stance or movements of the test subject and the sensing, and the data acquisition device can wirelessly transmit the plurality of measurements to the data analyzer to determine patterns of the stance or movements. Moreover, the data analyzer can perform a machine learning classification based on the plurality of measurements, wherein the machine learning classification can comprise perform ng support vector machine (SVM) for data training, performing ensemble boosting for increasing classification performance, performing leave-one-out standard for cross-validation (LOOCV) for inhibiting overfitting in classification, and performing ML based majority voting for reducing class-label noise in classification.

In another embodiment, a method for assessing stance or mobility of a test subject standing or moving using a CPS pressure based sensing system is provided. The method can comprise: obtaining a plurality of measurements with respect to the stance or movements of a test subject; and determining patterns of the stance or movements based on the plurality of measurements by performing machine learning (ML) based classification. Moreover, machine learning (MIL) based classification can comprise performing support vector machine (SVM) for data training, performing ensemble boosting for increasing classification performance, performing leave-one-out standard for cross-validation (LOOCV) for inhibiting overfitting classification, and performing ML based majority voting for reducing class-label noise in classification.

In another embodiment, a non-transitory computer readable medium comprising machine readable instructions executable by computing hardware for assessing stance or mobility of a test subject standing or moving is provided. The non-transitory computer readable medium can comprise instructions stored thereon that, when executed by a processor: obtain a plurality of measurements with respect to the stance or movements of the test subject; and determine patterns of the stance or movements based on the plurality of measurements by performing machine learning (ML) based classification. Moreover, the machine learning (ML) based classification can comprise performing support vector machine (SVM) for data training; performing ensemble boosting for increasing classification performance, performing leave-one-out standard for cross-validation (LOOCV) for inhibiting overfitting in classification, and performing ML based majority voting for reducing class-label noise in classification.

In some embodiments, for determining patterns of the stance or movements, the following steps can be performed before performing machine learning (ML) based classification: performing an automatic segmentation on the plurality of measurements, performing a metrics extraction on the results of the automatically segmentation; and performing a dimension reduction on the plurality of metrics extracted.

In certain embodiments, the plurality of measurements obtained by the at least one piezoresistive transducer can include kinetic or kinematic parameters of the stance or movements of the test subject.

In certain embodiments, the sensing and data acquisition device can include data storage and perform data analysis such as the functions of automatic segmentation in real-time.

DETAILED DESCRIPTION

Embodiments of the subject invention pertain to a cyberphysical system (CPS) pressure based sensing system to assess patterns of stance or mobility of an object standing or moving.

Figure 1:
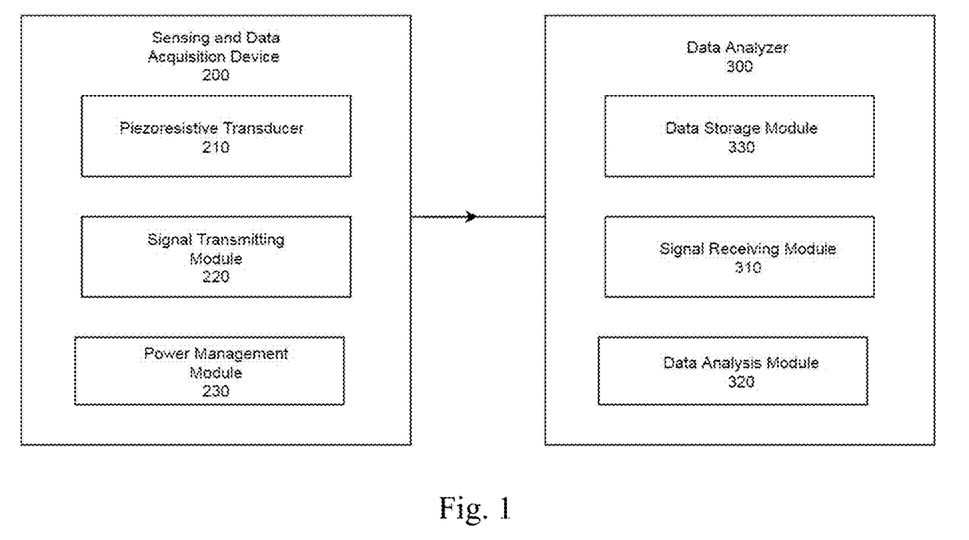
FIG. 1 is a schematic view of a CPS pressure based sensing system according to an embodiment of the subject invention.

FIG. 1 illustrates a CPS pressure based sensing system 100 according to an embodiment of the present invention. The CPS pressure based sensing system 100 can include: a sensing and data acquisition device 200 measuring kinetic or kinematics of a test subject; and a data analyzer 300 wirelessly communicating with the sensing and data acquisition device 200 and analyzing the measurements to evaluate patterns of the stance or movements of the test subject.

The sensing and data acquisition device 200 as shown in FIG. 1 can include at least one piezoresistive transducer 210, a signal transmitting module 220, and a power management module 230. The at least one piezoresistive pressure transducer 210 measures pressure or ground reaction forces and records changes in pressure or ground reaction forces across the surfaces of an object of the test subject (for example, a foot of a subject, such as a human subject), as well as kinetic or temporal features of the movements through inertial measurements.

In an embodiment, the sensing and data acquisition device 200 may include three Tekscan A301 piezoresistive pressure transducers installed at three different positions (for example, heel, medial lateral position, and toe) of an insole attached to the foot of the test subject, sensing forces between 0 to 445 Newtons with 3% linearity error, 2.5% repeatability and 4.5% hysteresis at 80% full force application.

Previous studies demonstrate that human locomotion examined using ground reaction forces has slow dynamics and a sampling frequency greater than 100 Hz is sufficient for measuring force, pressure, kinetic, or temporal parameters of the stance or movements of a human being test subject. Thus, the sensing and data acquisition device 200 can operate at a sampling frequency of, for example, 125 Hz, though embodiments are not limited thereto.

Figure 2:
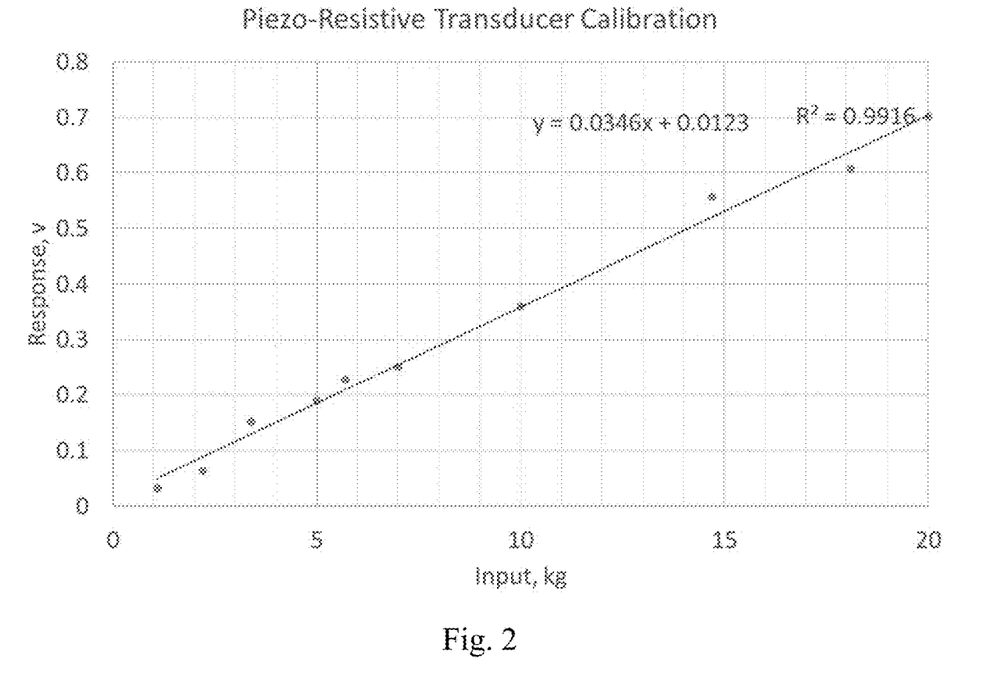
FIG. 2 is a plot diagram illustrating a relationship between input load and response voltage with respect to calibrations of a piezoresistive transducer, according to an embodiment of the subject invention.

To ensure accurate data sensing and recording, the piezoresistive pressure transducer 210 can be calibrated before measurements by applying known loads to the transducer and recording the output values to determine calibration relationships. FIG. 2 shows the results of a calibration of a piezoresistive pressure transducer using a dual source inverting Op-Amp setup. Specifically, the output voltage was determined to have a linear proportional relationship with the applied pressure, and a determination factor R2 having a 0.9916 coefficient was obtained indicating a good fit between the recorded responses and the representative equation.

Once the measurements are acquired by the piezoresistive pressure transducer 210, the signal transmitting module 220 transfers the measurement results to the data analyzer 300 such that the measurement results can be analyzed for determining the mobility patterns of the test subject.

Referring to FIG. 1, the sensing and data acquisition device 200 includes the power management module 230 for charging, voltage regulation, and temperature measurement operations. In an embodiment, the power management module 230 includes a power-path management IC, establishing bipolar power to feed a current to an amplifier (for example, an MCP6004 Op-Amp) through a voltage regulator (for example, a negative-output low-dropout linear voltage regulator). To allow a wider application of embodiments of the subject invention without hardware changes, the gain of the amplifier of the power management module can be made programmable. Moreover, the sensing and data acquisition device 200 may include data storage (not shown) and may perform data analysis (for example, functions of automatic segmentation as described below) onboard in real-time.

Figure 3A:
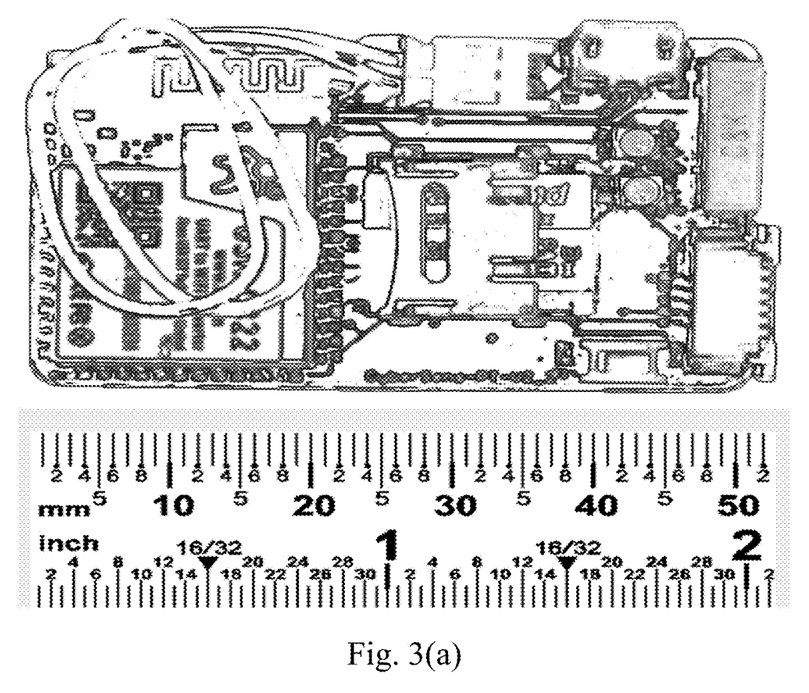
FIG. 3(a) shows an image of a prototype of a sensing and data acquisition device according to an embodiment of the subject invention.

FIG. 3(a) illustrates an image of a sensing and data acquisition device 200 according to an embodiment. The device 200 depicted in FIG. 3(a) was built based on a Texas Instruments Internet-of-Things prototyping platform having a 12-Bit ADC and 256 kB of RAM. On-board data recording was built-in with a micro-SD flash card capable of memory expansion up to 512 GB. This ancillary data acquisition route takes precedence when wireless data streaming is either not guaranteed or not needed. A CC3200 low-power Wi-Fi module was utilized for wireless communication. In alternative embodiments, breadboard working prototype or printed circuit board (PCB) prototype can be used for concept validation studies.

The sensing and data acquisition device shown in FIG. 3(a) can be employed for gait assessment of simulated LLD. In one particular experiment, nine human being test subjects, between 21 and 31 years of age, without previous musculoskeletal diagnoses or LLD, were asked to walk along a walkway that is 120 meters long at comfortable walking speeds while wearing the sensing and data acquisition device. Unaltered walking was considered symmetric and set as the ground truth against which sLLD are compared.

Figure 3B:
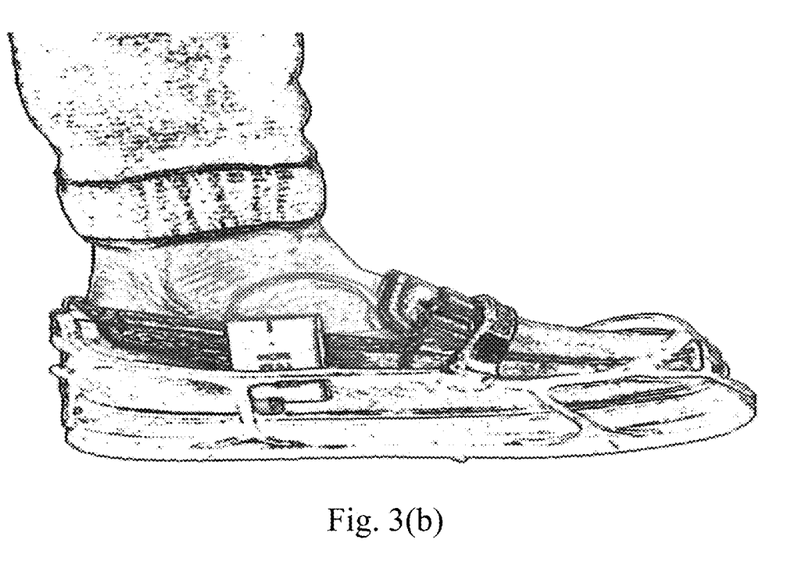
FIG. 3(b) shows an image of the sensing and data acquisition device of FIG. 3(a) and a foot of a human being test subject wearing an insole that has the prototype of the insole and sensing data acquisition device installed on a lateral part, while the test subject's gait is altered using a shoe spacer, according to an embodiment of the subject invention.

FIG. 3(b) illustrates simulated LLD by using a shoe spacer (for example, a shoe spacer from Evenup Shoe Balancer) that was worn on the right foot of one of the test subjects. The shoe spacer applied 2.5 cm of length inequality to the right foot and the sensing and data acquisition device was installed on an insole on a lateral part of the right foot. Being able to control the amount of LLD ensures that the detection is effective for the targeted sLLD and not of other gait abnormalities.

Referring back to FIG. 1, to evaluate the patterns of the stance or movements of the test subjects, the measurement results acquired by the sensing and data acquisition device 200 can be transferred to the data analyzer 300. The data analyzer 300 can include a signal receiving module 310, a data storage module 330, and a data analysis module 320. The signal receiving module 310 receives data or signals transmitted from the signal transmitting module 220, the data analysis module 320 performs data analysis steps of S510-S540 as described in further detail below with reference to FIG. 6, and the data storage module 330 stores the data or signals received and data generated during the data analysis.

Figure 4:
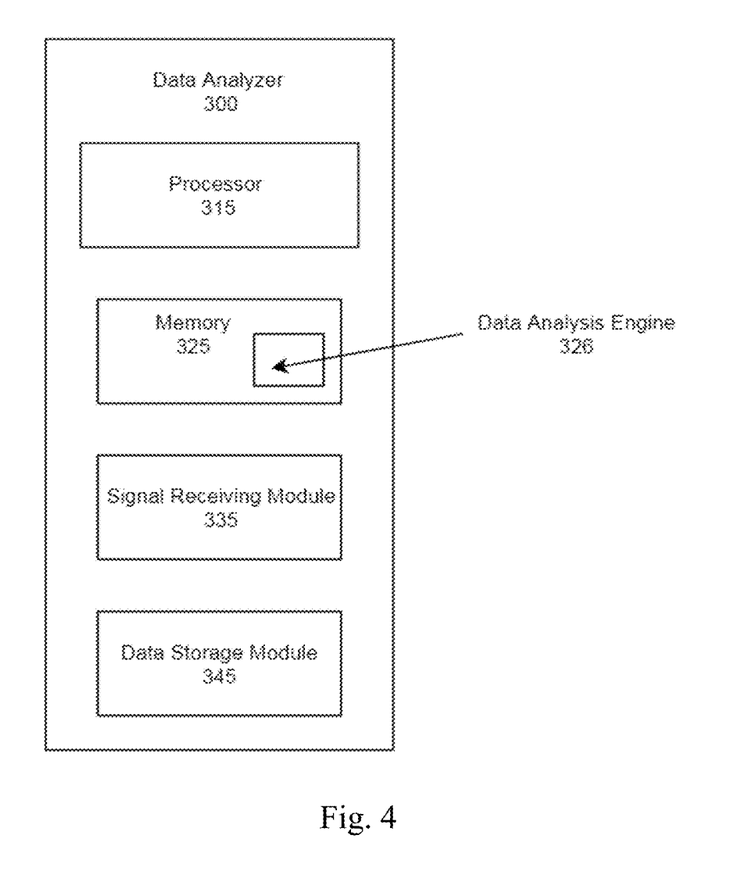
FIG. 4 is a schematic view of an alternative implementation of the data analyzer of the CPS pressure based sensing system shown in FIG. 1, according to an embodiment of the subject invention.

In alternative embodiments, the data analyzer 300 can perform its functionalities based on another implementation as illustrated by FIG. 4. In contrast to FIG. 1, the data analyzer 300 shown in FIG. 4 can include a processor 320 and a memory 325 instead of the data analysis module 320. The memory 325 can comprise executable-code components of a data analysis engine 326 for execution by the processor 320. The data analysis engine 326 performs the data analysis steps of S510-S540 as described in further detail below with reference to FIG. 6. In this respect, the terms "executable" or "for execution" refer to forms of executable-code that can ultimately be run or executed by the processor 320, whether in source, object, machine, or other form.

As discussed above, a data analysis engine 326 may be embodied, at least in part, by software or executable-code components for execution by general purpose hardware. Alternatively the same can be embodied in dedicated hardware or a combination of software, general, specific, and/or dedicated purpose hardware. If embodied in such hardware, each can be implemented as a circuit or state machine, for example, that employs any one of or a combination of a number of technologies. These technologies can include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc.

Figure 5:
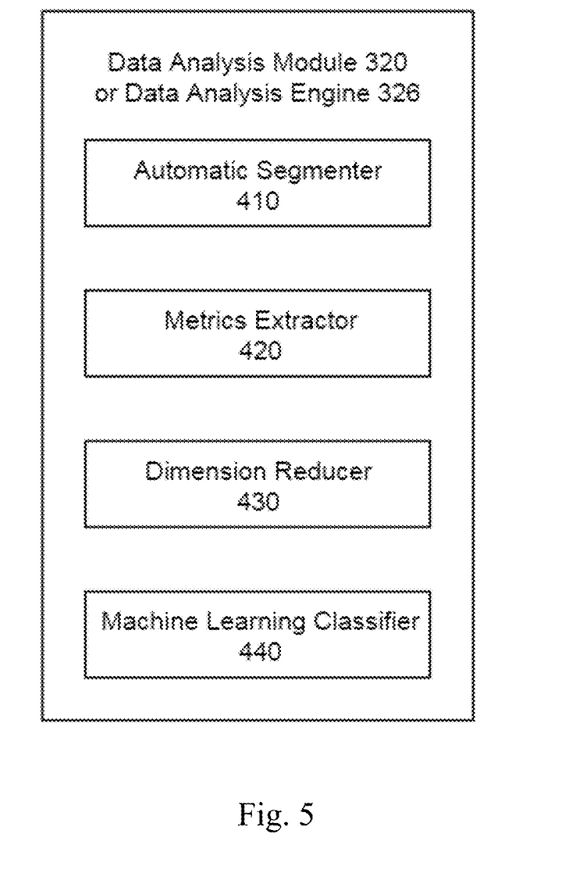
FIG. 5 is a schematic view of a data analysis module according to an embodiment of the subject invention.

Referring to FIG. 5, the data analysis module 320 or the data analysis engine 326 can comprise an automatic segmenter 410, a metrics extractor 420, a dimension reducer 430, or a machine learning classifier 440, or a combination of any number of them, according to various embodiments of the subject invention.

Figure 6:
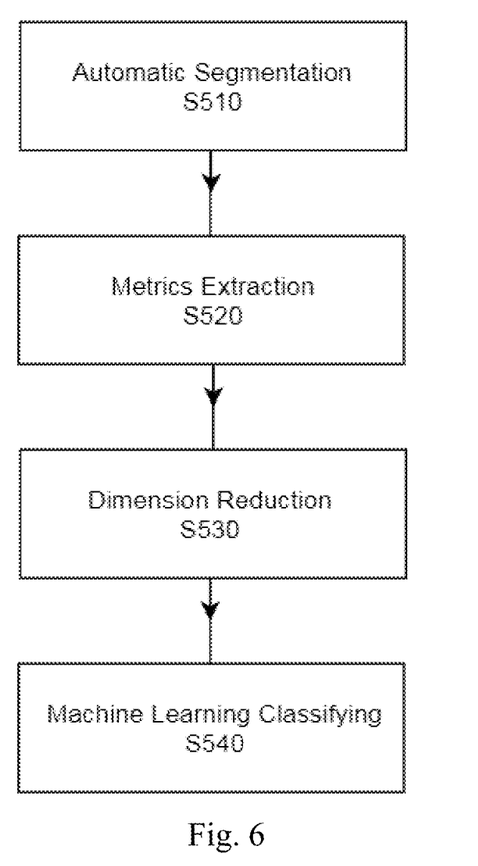
FIG. 6 is a flow diagram illustrating operations of a data analysis module according to an embodiment of the subject invention.

The operations of the data analysis module 320 or the data analysis engine 326 are illustrated by FIG. 6, according to various embodiments of the subject invention.

Automatic Segmentation

First, at step S510, an automatic segmentation is performed by the automatic segmenter 410, extracting a plurality of representative features from the measurement results acquired by the piezoresistive transducer 210 and automatically segmenting the measurement results into distinguishable phases. For example, for assessing asymmetry of gaits of sLLD, five representative features including heel contact, maximum heel contact, midstance, maximum toe contact, and toe off can be extracted. Then gait cycles are segmented into four distinguishable phases including heel strike, flat foot, heel off, and swing, based on these representative features.

Specifically, the automatic segmenter 410 employs a threshold value for extracting the representative features. The threshold value can be manually defined by a user or automatically defined by the automatic segmenter 410. If a measurement is determined to be greater than the threshold value, a value of 1 is assigned by the automatic segmenter 410 to a binary signal associated with the measurement. On the other hand, if a measurement is determined to be smaller than the threshold value, a value of 0 is assigned to the binary signal associated with the measurement.

Figure 7:
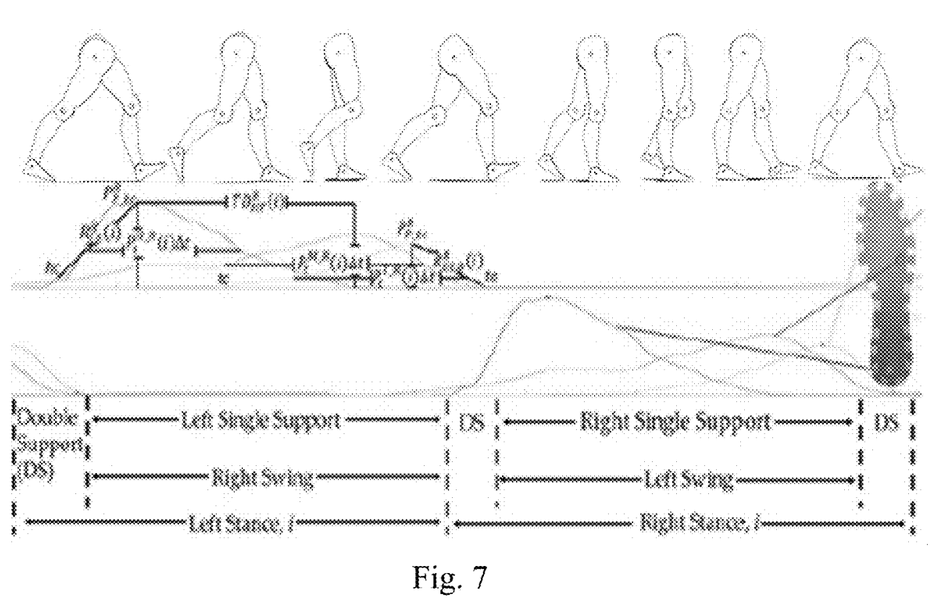
FIG. 7 a schematic view of locomotion phases and selected metrics' association with respect to features and time of ground reaction force, according to an embodiment of the subject invention.

Next, the automatic segmenter 410 utilizes the binary signals to differentiate phases of the stance or movements of the test subject. As illustrated in FIG. 7, a positive spike of the binary signal indicates a feature of heel contact while a negative spike of the binary signal indicates a feature of toe off. Further, the representative features such as heel contact or toe off are used to determine start or stop of the stance or swing phases. Similarly, the feature of midstance is approximated by measuring a halfway point between the feature of heel contact and the feature of toe off, the feature of maximum heel contact is extracted by evaluating the maximum pressure value between the feature of heel contact and the feature of midstance, and the feature of maximum toe contact is extracted by evaluating the maximum pressure value between the midstance and the toe off. From these two pressure peaks, the loading response, pre-swing, and flat foot phases are thus determined.

In FIG. 7, three piezoresistive pressure transducers were installed at three different positions of the insole wored by the test subject, wherein the lower circle indicates the position of a first piezoresistive pressure transducer at the heel, the middle circle indicates a second piezoresistive pressure transducer at the medial lateral position, and the upper circle indicates a third piezoresistive pressure transducer at the toe position.

Metrics Extraction

Upon completion of the automatic segmentation, a metrics extraction can be performed by the metrics extractor 420 at step S520, extracting a plurality of metrics from the features obtained by the automatic segmentation.

In various embodiments, some or all of thirteen metrics can be extracted, including:

(1) difference in single stance time duration ("stance duration");
(2) difference in mean stance pressure ("heel stance pressure");
(3) medial lateral stance pressure;
(4) toe stance pressure;
(5) pressure distribution from medial lateral to heel;
(6) pressure distribution from medial lateral to toe;
(7) first peak pressure;
(8) time to first peak;
(9) second peak pressure;
(10) time from second peak to toe off;
(11) time between maximum cycle peaks;
(12) loading rate; and
(13) push off rate.

The definition and significance of each of the thirteen metrics will be presented with details below.

The first metric of difference in single stance time duration ("stance duration"), $\Delta TD_s(i)$, is defined by Equation (1) to show the discrepancy between the right foot $TD_s^R(i)$ and left foot $TD_s^L(i)$.

$$\Delta TD_s(i) = TD_s^R(i) - TD_s^L(i) = (T_{to}^R(i) - T_{hc}^R(i)) - T_{to}^L(i) - T_{hc}^L(i)) \quad (1)$$

where i is the i-th single support within a gait cycle, hc is the heel contact, and to is toe off.

In the sLLD assessment experiment, this metric of stance duration can be utilized to determine whether a limping exists. The limping in a sLLD experiment may originate from the added foot spacer on the right leg and less weight acceptance on the left leg.

The second to fourth metrics of difference in mean stance pressure ("heel stance pressure"), medial lateral stance pressure, and toe stance pressure are defined by Equations (2)-(4), respectively. In particular, the difference in mean stance pressure is calculated between midstance and terminal stance, when the body weight of the test subject is completely shifted from the heel to the toe, showing the right to left comparison between total pressure at each piezoresistive pressure transducer during each stance time on heel $\Delta|P_{h\_s}$, on medial lateral $\Delta P_{M\_s}$, and on toe $\Delta P_{Ts}$.

$$\Delta P_{H\_s}(i) = \frac{P_{H\_s}^R(i) - P_{H\_s}^L(i)}{P_{H\_s}^R(i) - P_{H\_s}^L(i)} = \frac{\frac{\sum_{t=hc}^{tc} P_t^{H\_R}(i)\Delta T}{T_{tc}^R(i) - T_{hc}^R(i)} - \frac{\sum_{t=hc}^{tc} P_t^{H\_L}(i)\Delta T}{T_{tc}^L(i) - T_{hc}^L(i)}}{\frac{\sum_{t=hc}^{tc} P_t^{H\_R}(i)\Delta T}{T_{tc}^R(i) - T_{hc}^R(i)} + \frac{\sum_{t=hc}^{tc} P_t^{H\_L}(i)\Delta T}{T_{tc}^L(i) - T_{hc}^L(i)}} \quad (2)$$

$$\Delta P_{M\_s}(i) = \frac{P_{M\_s}^R(i) - P_{M\_s}^L(i)}{P_{M\_s}^R(i) + P_{M\_s}^L(i)} = \frac{\frac{\sum_{t=hc}^{tc} P_t^{M\_R}(i)\Delta T}{T_{tc}^R(i) - T_{hc}^R(i)} - \frac{\sum_{t=hc}^{tc} P_t^{M\_L}(i)\Delta T}{T_{tc}^L(i) - T_{hc}^L(i)}}{\frac{\sum_{t=hc}^{tc} P_t^{M\_R}(i)\Delta T}{T_{tc}^R(i) - T_{hc}^R(i)} + \frac{\sum_{t=hc}^{tc} P_t^{M\_L}(i)\Delta T}{T_{tc}^L(i) - T_{hc}^L(i)}} \quad (3)$$

$$\Delta P_{T\_s}(i) = \frac{P_{T\_s}^R(i) - P_{T\_s}^L(i)}{P_{T\_s}^R(i) + P_{T\_s}^L(i)} = \frac{\frac{\sum_{t=hc}^{tc} P_t^{T\_R}(i)\Delta T}{T_{tc}^R(i) - T_{hc}^R(i)} - \frac{\sum_{t=hc}^{tc} P_t^{T\_L}(i)\Delta T}{T_{tc}^L(i) - T_{hc}^L(i)}}{\frac{\sum_{t=hc}^{tc} P_t^{T\_R}(i)\Delta T}{T_{tc}^R(i) - T_{hc}^R(i)} + \frac{\sum_{t=hc}^{tc} P_t^{T\_L}(i)\Delta T}{T_{tc}^L(i) - T_{hc}^L(i)}} \quad (4)$$

where PH is the pressure on heel, PM is the pressure on medial lateral, PT is pressure on toe and tc stands for toe contact.

The fifth and sixth metrics of pressure distribution from medial lateral to heel and pressure distribution from medial lateral to toe are defined by Equations (5) and (6), respectively. In particular, these two metrics respectively show the difference in sagittal pressure distribution; on medial-lateral to heel $\Delta RP_{M-H}$ and on medial-lateral to toe $\Delta RP_{H-T}$, indicating the asymmetry from left to right pressure, while the body weight of the test subject is shifting from the heel to the toe.

$$\Delta RP_{M-H}(i) = \frac{RP_{M-H}^R(i)}{RP_{M-H}^L(i)} = \frac{\frac{\sum_{t=hc}^{tc} P_t^{M\_R}(i)\Delta T}{\sum_{t=hc}^{tc} P_t^{H\_R}(i)\Delta T}}{\frac{\sum_{t=hc}^{tc} P_t^{M\_L}(i)\Delta T}{\sum_{t=hc}^{tc} P_t^{H\_L}(i)\Delta T}} \quad (5)$$

$$\Delta RP_{M-T}(i) = \frac{RP_{M-T}^R(i)}{RP_{M-T}^L(i)} = \frac{\frac{\sum_{t=hc}^{tc} P_t^{M\_R}(i)\Delta T}{\sum_{t=hc}^{tc} P_t^{T\_R}(i)\Delta T}}{\frac{\sum_{t=hc}^{tc} P_t^{M\_L}(i)\Delta T}{\sum_{t=hc}^{tc} P_t^{T\_L}(i)\Delta T}} \quad (6)$$

The seventh and eighth metrics of first peak pressure and time to first peak are defined by Equations (7) and (8), respectively. In particular, these two metrics respectively show the difference in peak heel contact pressure $\Delta PP$-hc and difference in peak toe contact pressure $\Delta PP$-tc, measured at terminal stance, indicating the pressure asymmetry during maximal pressure exertion.

$$\Delta P_{P\_hc}(i) = \frac{P_{P\_hc}^R(i) - P_{P\_hc}^L(i)}{P_{P\_hc}^R(i) + P_{P\_hc}^L(i)} = \frac{\max\{P_{hc}^R(i)\} - \max\{P_{hc}^L(i)\}}{\max\{P_{hc}^R(i)\} + \max\{P_{hc}^L(i)\}} \quad (7)$$

$$\Delta P_{P\_tc}(i) = \frac{P_{P\_tc}^R(i) - P_{P\_tc}^L(i)}{P_{P\_tc}^R(i) + P_{P\_tc}^L(i)} = \frac{\max\{P_{tc}^R(i)\} - \max\{P_{tc}^L(i)\}}{\max\{P_{tc}^R(i)\} + \max\{P_{tc}^L(i)\}} \quad (8)$$

The ninth and tenth metrics of second peak pressure and time from second peak to toe off are defined by Equations (9) and (10). These two metrics respectively show the difference in the heel reposition time $\Delta THR$ and in the toe reposition time $\Delta TTR$, indicating the asymmetry the time needed to achieve maximum loading response after initial heel contact, from right to left foot.

$$\Delta T_{TR}(i) = T_{HR}^R(i) - T_{HR}^L(i) = (T_{P\_hc}^R(i) - T_{hc}^R(i)) - T_{P\_hc}^L(i) - T_{hc}^L(i)) \quad (9)$$

$$\Delta T_{TR}(i) = T_{TR}^R(i) - T_{TR}^L(i) = (T_{P\_tc}^R(i) - T_{tc}^R(i)) - T_{P\_tc}^L(i) - T_{tc}^L(i)) \quad (10)$$

The eleventh metric of time between maximum cycle peaks is defined by Equation (11). This metric shows the difference in the time duration from heel to toe displacement $\Delta TDHT$, indicating the asymmetry of duration between maximum pressure exertion, by heel and toe, between the right and left foot.

$$\Delta T_{TR}(i) = T_{TR}^R(i) - T_{TR}^L(i) = (T_{P\_tc}^R(i) - T_{tc}^R(i)) - (T_{P\_tc}^L(i) - T_{tc}^L(i))$$

$$\Delta TD_{HT}(i) = TD_{HT}^R(i) - TD_{HT}^L(i) = (T_{Ptc}^R(i) - T_{Phc}^R(i)) - (T_{Ptc}^L(i) - T_{Phc}^L(i)) \quad (11)$$

The twelfth and thirteenth metrics of loading rate and push off rate are defined by Equations (12) and (13). In particular, these two metrics show the ratio difference of loading $\Delta RLE$ and unloading effect $\Delta RULD$, indicating how much force is exerted during heel contact and how much force is exerted during toe-off as compared between right and left foot, in the case of loading highly depending on the preceding contralateral toe off behavior.

$$\Delta R_{LE}(i) = \frac{R_{LE}^R(i) - R_{LE}^L(i)}{R_{LE}^R(i) - R_{LE}^L(i)} = \frac{\frac{P_{P\_hc}^R(i) - P_{hc}^R(i)}{T_{P\_hc}^R(i) - T_{hc}^R(i)} - \frac{P_{P\_hc}^L(i) - P_{hc}^L(i)}{T_{P\_hc}^L(i) - T_{hc}^L(i)}}{\frac{P_{P\_hc}^R(i) - P_{hc}^R(i)}{T_{P\_hc}^R(i) - T_{hc}^R(i)} + \frac{P_{P\_hc}^L(i) - P_{hc}^L(i)}{T_{P\_hc}^L(i) - T_{hc}^L(i)}} \quad (12)$$

-continued $$\Delta R_{ULD}(i) = \frac{R_{ULD}^R(i) - R_{ULD}^L(i)}{R_{ULD}^R(i) - R_{ULD}^L(i)} = \frac{\frac{P_{P\_tc}^R(i) - P_{tc}^R(i)}{T_{P\_tc}^R(i) - T_{tc}^R(i)} - \frac{P_{P\_tc}^L(i) - P_{tc}^L(i)}{T_{P\_tc}^L(i) - T_{tc}^L(i)}}{\frac{P_{P\_tc}^R(i) - P_{tc}^R(i)}{T_{P\_tc}^R(i) - T_{tc}^R(i)} + \frac{P_{P\_tc}^L(i) - P_{tc}^L(i)}{T_{P\_tc}^L(i) - T_{tc}^L(i)}} \quad (13)$$

Dimensionality Reduction

Since the metrics extracted as illustrated above are not necessarily uncorrelated, the dimension reducer 430 performs a dimensionality reduction at step S530. In particular, the dimension reducer 430 determines which metrics have larger inter-class variations; i.e., larger differences between normal and LLD classes, to reduce or eliminate the overfitting in succeeding LLD classification as well as to improve computational efficiency.

In one embodiment, a linear discriminant analysis (LDA) such as Fisher's LDA is performed at step S530 to reduce or eliminate correlated features that do not provide classification improvement. Specifically, Fisher's LDA is utilized for its capability to select discriminant variables based on separability between classes, resulting in a reduction or an elimination of inclusions of high-dimensional data containing correlated variables that may introduce collinearity and thus the overfitting issue.

At step S530, the dimension reducer 430 also ranks the metrics extracted at step S520 by maximization between class differences based on t-test results, thereby determining which metrics are best for separation of two classes and are thus more accurate for results assessment (for example, detection of sLLD).

Machine Learning (ML) Classifying/Classification

Upon completion of the dimensionality reduction, the machine learning (ML) classifier 440 starts performing a machine learning classification at step S540.

Figure 8:
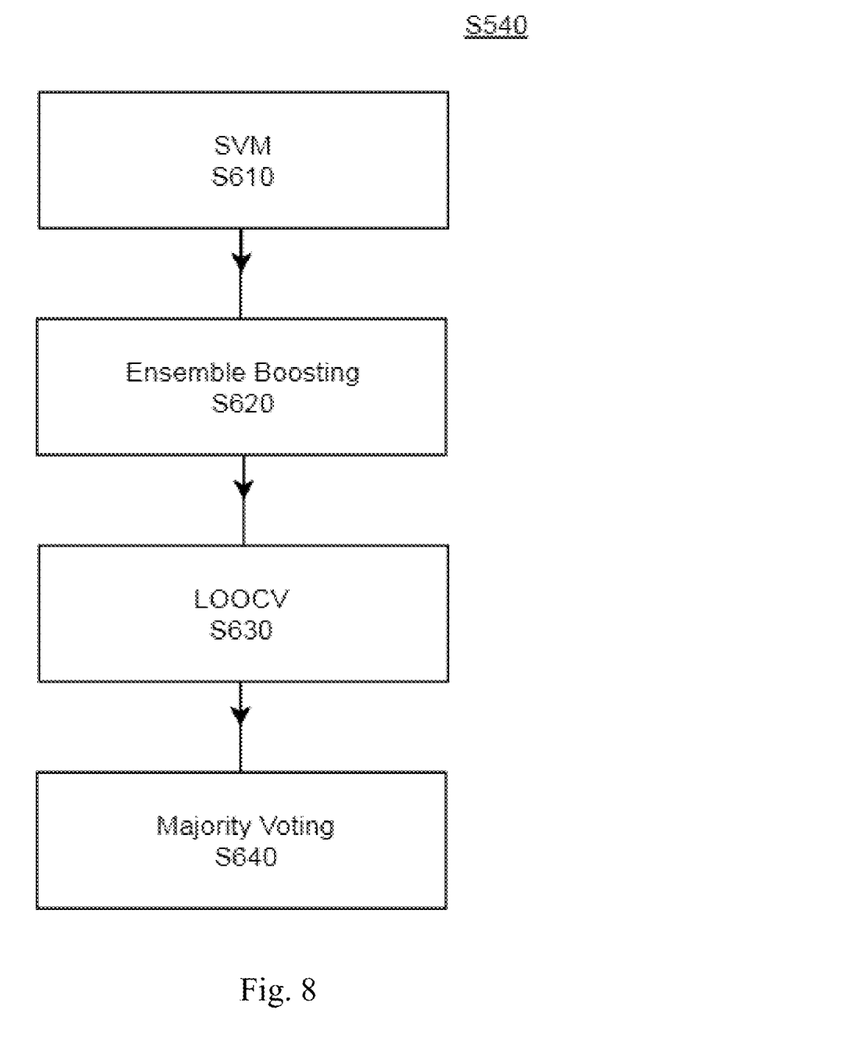
FIG. 8 is a flow diagram illustrating operation steps of a machine learning classification according to an embodiment of the subject invention.

FIG. 8 illustrates operations of the machine learning (ML) classifier 440 according to an embodiment of the subject invention. The machine learning classifier 440 may perform a support vector machines (SVM) step that fits an optimal hyperplane between datasets; an ensemble boosting step at which a meta-algorithm on decisions trees and discriminant analysis learners is performed to improve classification by adapting weights to sort features to generate state prediction models; a supervised training and data processing step by LOOCV; or a step of evaluating the classification results to find an average step count from which a majority voting can be applied to further improve classification; or a combination of any number of these steps, according to various embodiments of the subject invention.

Support Vector Machines (SVM)

At the SVM step S610, training data are used to create separating vectors based on neighboring data. In the case of non-linearly separable data, a kernel is implemented to map data to higher dimensional feature space, where data is linearly separated and a hyper-plane is returned to the original space for classification. In some embodiments, linear, Gaussian, or polynomial kernel may be applied to achieve better assessment performance.

Ensemble Boosting

At the ensemble boosting step S620, an ensemble learning is performed based on the training of several low accuracy classification techniques for building an incrementally better performing classifier.

For example, Adaptive Boost (AdaBoost) can be used to apply weights to miss-classified samples, resulting in a reduction or an elimination of errors in subsequent iterations. Moreover, the ensemble boosting can produce better classifier functions based on statistical averaging from votes provided by individual hypotheses, leading to a good approximation of the true classification hypothesis. Furthermore, the ensemble boosting may employ a hypothetical function based on an average of the different local maxima to solve the issue of convergence at different local maxima. As a result, the hypotheses averaging allows for a creation of new classifiers that may not be produced based only on the training data and the trends represented by them.

Supervised Training and Data Processing by LOOCV

A leave-one-out standard for cross-validation (LOOCV) is performed at the LOOCV step S630 to ensure training is completely separate from the testing data. This step includes training the classifiers with all subjects except for the one whose data will be used for testing. As a result, the classification is subject-independent and the issue of overfitting is reduced or eliminated, increasing the usefulness of the results. However, less accurate classifiers can be generated due to the high variability of gait within and between subjects.

Specifically, at the LOOCV step S630, training data S={(x1,y1) . . . (xn,yn)} from the all-but-one subject, with input xi and class labels yi∈{−1(Normal), 1(LLD)}, is offered to the learners. The learners are then tuned by branch size or iterative count and learning rate. This procedure leads to convergence of correctly labeled samples, but increases computation time.

Majority Voting for Gait Cycle Polling

A majority voting is performed at the step S640 to average consecutive steps and their interactions, thereby finding a minimum step count from which a proper result assessment, such as an estimation of sLLD, can be made. First, the consecutive cycles are selected from the automatic segmentation and used in the voting rounds. Next, a majority voting is performed on the first round of classifiers in groups of, for example, single (non-voting), 3, and 5 gait cycles, to SVMs such as polynomial and Gaussian, as well as the ensemble AdaBoosting discriminant and the tree learners.

Several performance benefits can be obtained as a result. First, polling of successive cycles for the possibility of sLLD, as consecutive cycles may undergo a cancellation effect, or adaptation due to the applied sLLD is achieved. Second, the class-label noise inherent to AdaBoost learners, whose weighted voting favors misclassified samples in its iterative process leading to overfitting, is reduced or eliminated.

Performance Analysis

Accuracy, sensitivity, and false positive rate as defined by Equations (14)-(16) are used to evaluate the effectiveness of the result assessment (for example, detection of sLLD). In Equations (14)-(16), TP represents the number of correctly detected sLLD samples, TN represents the number of correctly classified normal samples, FP represents the number of normal samples incorrectly detected as sLLD, and FN represents the number of sLLD samples incorrectly detected as normal. Moreover, Matthews correlation coefficient (MCC) is used to gauge the agreement between target and predictions thus measuring the quality of the binary classifications varying between −1 for perfect disagreement and 1 for perfect agreement.

$$\text{Accuracy} = \frac{TP + TN}{TP + FP + TN + FN} \times 100\% \quad (14)$$

-continued $$\text{Sensitivity} = \frac{TP}{TP + FN} \times 100\% \quad (15)$$

$$\text{False Positive Rate} = \frac{FP}{FP + TP} \times 100\% \quad (16)$$

$$\text{Matthews Correlation Coefficient} = \quad (17)$$
$$\frac{TP \times TN - FP \times FN}{\sqrt{(TP + FP)(TP + FN)(TN + FP)(TN + FN)}}$$

TABLE 1

Feature ranking based on SVM classification

| Metric | Equation | Single Vote Accuracy (±SD) | T-test P-Value | Ranking |
|---|---|---|---|---|
| Loading Rate, $\Delta R_{LE}$ | (12) | 63.5 (9.5) | 2.87e-30[1] | 1 |
| Time to First Peak, $\Delta P_{p\_tc}$ | (8) | 64.6 (13) | 1.58e-24[2] | 2 |
| Stance Duration, $\Delta TD_s$ | (1) | 66.9 (14.3) | 5.89e-23[3] | 3 |
| Push Off Rate, $\Delta R_{ULD}$ | (13) | 54.9 (9.1) | 2.36e-09 | 4 |
| Heel Stance Pressure, c | (2) | 46.5 (11.9) | 9.91e-09 | 5 |
| First Peak Pressure, $P_{p\_hc}$ | (7) | 57.1 (14.1) | 4.35e-08 | 6 |
| Medial Lateral Stance Pressure, $\Delta P_{M\_s}$ | (3) | 48.2 (16.4) | 1.94e-05 | 7 |
| Toe Stance Pressure, $\Delta P_{T\_s}$ | (4) | 49.9 (4.9) | 3.62e-05 | 8 |
| Second Peak Pressure, $\Delta T_{HR}$ | (9) | 51.3 (2.4) | 4.11e-05 | 9 |
| Pressure Distribution Form Medial Lateral to Heel, $\Delta RP_{M-H}$ | (5) | 56.9 (17.6) | 3.02e-04 | 10 |
| Time from Second Peak to Toe Off, $\Delta T_{TR}$ | (10) | 52.3 (4.6) | 8.16e-04 | 11 |
| Time Between Maximum Cycle Peaks, $\Delta TD_{HT}$ | (11) | 52.9 (13.7) | 1.25e-02 | 12 |
| Pressure Distribution From Medial Lateral to Toe, $\Delta RP_{M-T}$ | (6) | 39.6 (12.3) | 4.18e-01 | 13 |

Table 1 summarizes the metrics selection after the LDA and the ranking based on statistical significance between classes. The testing accuracy shown in Table 1 is the average of all nine test subjects for a polynomial SVM classifier. The three best performing metrics are the loading rate defined by Equation (12), the time to first peak defined by Equation (8), and the stance time defined by Equation (1), wherein the loading rate is a kinetic metric and the time to first peak and the stance time are both temporal metrics.

In an experiment, the metric of loading rate can be extracted based on measurements acquired by a single piezoresistive pressure transducer installed at the heel of the foot. Moreover, the metric of stance time can be extracted based on measurements acquired by the piezoresistive pressure transducer installed at the heel and by another piezoresistive pressure transducer installed at the toe. Furthermore, the metric of time to first peak can be extracted based on measurements acquired by the same piezoresistive pressure transducer used for the metric of loading rate.

According to Table 1, the metrics are ranked from the best to the worst performance as follows: loading rate, time to first peak, stance duration, push off rate, heel stance pressure, first peak pressure, medial lateral stance pressure, toe stance pressure, second peak pressure, pressure distribution form medial lateral to heel, time from second peak to toe off, time between maximum cycle peaks, and pressure distribution from medial lateral to toe.

TABLE 2

Data Set Sample Count

| Participant | Normal | sLLD |
|---|---|---|
| 1 | 41 | 61 |
| 2 | 56 | 57 |
| 3 | 39 | 44 |
| 4 | 42 | 45 |
| 5 | 57 | 57 |
| 6 | 49 | 49 |
| 7 | 53 | 53 |
| 8 | 42 | 48 |
| 9 | 58 | 60 |

Table 2 summarizes data set sample count for each subject during each test. It can be seen from Table 2 that the resulting data set was made up of 49±7 samples for normal walking and 53±6 samples for sLLD walking.

TABLE 3

Classifier Results for joint sensitivity, false positive rate, and accuracy within different ML types, number of features used, and majority voting results

| Machine Learning Classifier | Metrics | All features (No LDA) | | | 3 features | | | 1 feature | | |
|---|---|---|---|---|---|---|---|---|---|---|
| Polynomial | Majority Vote | 1 | 3 | 5 | 1 | 3 | 5 | 1 | 3 | 5 |
| SVM | Sens | 77.1 | 50.4 | 64.8 | 80.9 | 58.8 | 70.6 | 80.8 | 62.1 | 72 |
|  | (±SD) | (14.3) | (26.7) | (22.0) | (15.4) | (29.3) | (30.1) | (17) | (30.2) | (29.9) |
|  | Fls Pos Rt | 28.7 | 7.3 | 10.4 | 13.5 | 0.7 | 1.2 | 17.3 | 2.8 | 3.7 |
|  | (±SD) | (23.7) | (16.4) | (21.9) | (8.5) | (2) | (3.5) | (13.6) | (7.9) | (10.5) |
|  | Accuracy | 74.2 | 71.6 | 77.2 | 83.7 | 79 | 84.7 | 81.7 | 79.7 | 84.2 |
|  | (±SD) | (13.8) | (17.9) | (17.7) | (9.1) | (14.4) | (14.5) | (10.2) | (14.5) | (14.1) |
|  | MCC | 0.49 | 0.49 | 0.58 | 0.74 | 0.72 | 0.82 | 0.75 | 0.74 | 0.84 |
|  | (±SD) | (0.28) | (0.35) | (0.35) | (0.19) | (0.17) | (0.25) | (1.7) | (14) | (0.25) |
| AdaBoost Tree | Sens | 75.8 | 46.9 | 62.8 | 82.8 | 64.3 | 75 | 86.2 | 69.4 | 836.6 |
|  | (±SD) | (14.2) | (27.9) | (27.6) | (13.3) | (25.1) | (24.3) | (11.3) | (22.1) | (18.4)[1] |
|  | Fls Pos Rt | 26.5 | 5.6 | 7.5 | 20.8 | 2.8 | 6.2 | 18.2 | 1.4 | 3.9 |
|  | (±SD) | (22.1) | (11.6) | (16.0) | (16.3) | (7.9) | (14) | (10.8) | (3.9) | (5.5) |
|  | Accuracy | 74.7 | 70.6 | 77.6[1,2] | 81 | 80.8 | 84.4 | 84 | 84 | 89.9 |
|  | (±SD) | (9.3) | (11.2) | (10.6) | (10.6) |  | (11.6) | (8.9) | (10.6) | (9.1)[2] |
|  | MCC | 0.52 | 0.50 | 0.61 | 0.73 | 0.69 | 0.85 | 0.75 | 0.68 | 0.86 |
|  | (±SD) | (0.18) | (0.19) | (0.24) | (0.18) | (0.22) | (0.21) | (0.18) | (20) | (0.21) |

TABLE 3-continued

Classifier Results for joint sensitivity, false positive rate, and accuracy within different ML types, number of features used, and majority voting results

| Machine Learning Classifier | Metrics | All features (No LDA) | | | 3 features | | | 1 feature | | |
|---|---|---|---|---|---|---|---|---|---|---|
| Polynomial | Majority Vote | 1 | 3 | 5 | 1 | 3 | 5 | 1 | 3 | 5 |

[1,2]Using only stance duration for classification, the highest sensitivity and overall accuracy for all ML classifiers was achieved using Ensemble AdaBoost Decision Trees with a 5-vote majority rating.

Table 3 summarizes classifier results for joint sensitivity, false positive rate, and accuracy across polling. It is noted that when only stance duration was used for classification, the highest sensitivity and overall accuracy for all ML classifiers were achieved by Ensemble AdaBoost Decision Trees with a 5-vote majority rating. According to Table 3, results of training performed with the three highest ranked metrics are shown in the columns under "3 features" and results of training performed with only loading rate are shown in the columns under "1 feature".

When the three highest ranked metrics are used for result assessment, the overall accuracy was higher using 5-vote over no-vote polling with an average increase of 1.5%. Similarly, when the false positive rate is used for result assessment, an overall decrease of 67.3% after 5 votes over single voting is achieved. However, as shown in Table 3, sensitivity is decreased by 5.4% after 5 votes in comparison to non-voting. It is noted that for all classifiers using the combinations of the three highest ranked metrics, the sensitivity suffered the largest decrease when attempting to decide based on 3 votes as opposed to 5.

Within individual ML classifiers, polling 5 votes over no voting when using three highest ranked metrics as opposed to one metric obtained the best accuracy increase and smaller sensitivity decrease for both Gaussian and polynomial SVM learners. Meanwhile, the largest false positive decreases were achieved by the two SVM learners over 5-poll voting, when using only one highest of the three ranked metric as opposed to using all three highest ranked metrics. For tests with both Ensemble AdaBoost learners, the results showed the greatest accuracy increase after voting using only one of the three highest ranked metrics, with the largest decrease in the false positives and the smallest decrease in the sensitivity. In addition, the average MCC for all classifiers after the LDA was determined to be 0.76, indicating a good overall binary prediction.

The overall best performing classifier was the Ensemble AdaBoost Tree, which, after polling with 5 votes, achieved an overall accuracy increase by 3.4% to 89.9%, a decrease in false positives by 64.7% to 3.9%, the smallest overall sensitivity decrease by 1.5% to 83.6%, and an MCC of 0.86.

The results shown above demonstrate that even with a relative small population of test subjects, the CPS pressure based sensing system of embodiments of the subject invention achieves an accurate and reliable detection of sLLD. The evaluation of different classifiers and the incorporation of majority voting allow for reducing or eliminating uncorrelated errors inherent to gaits between test subjects and gaits of the same test subject.

For a particular ML classifier implemented for sLLD detection, an increase in sensitivity and accuracy and a decrease in false positives with majority voting may depend on the number of metrics used for gait assessment. For example, in the case of using both discriminant and tree ensemble classifiers, a single highest ranked metric was sufficient to provide the best classification models after voting, whereas in the case of using both polynomial and Gaussian SVM, the largest increase in performance after voting for accuracy and sensitivity is obtained when all three highest ranked metrics are utilized.

By performing majority voting on the results of the weighted polling by AdaBoost, the class-label noise issue inherent to AdaBoost Ensembles is overcome. This is achieved by reducing or eliminating uncorrelated errors of individual classifiers by averaging.

Because performance of a classifier is highly dependent on the features chosen, linear discriminant analysis is used for dimensionality reduction based on correlation and maximization of class separation. As shown in Table 3, a three-dimensional training set was sufficient to differentiate between states of walking. It is noted that there is an association between classifier performance and low metric count. This cancellation effect may be caused by high correlation between metrics or differing adaptive responses in gait by the addition of the foot spacer.

Results as discussed above indicate that the CPS pressure based sensing system of embodiments of the subject invention is an effective, reliable, simple-to-use, and low-cost option for the mobility assessment including detection of low-level asymmetry in LLD or sLLD.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

In an embodiment, a cyber-physical system (CPS) pressure based sensing system for assessing stance or mobility of an object standing or moving can comprise: a sensing and data acquisition device comprising at least one piezoresistive transducer, and a data analyzer in operable communication with the sensing and data acquisition device. The sensing and data acquisition device can further comprise: a wireless communication module for wirelessly transmitting the measurements to the data analyzer; and a power management module. The at least one piezoresistive transducer can be configured to obtain a plurality of measurements with respect to the stance or movements of the object. The data analyzer can comprise: a signal receiving module configured to wirelessly receive the measurements from the sensing and data acquisition device; a data storage module; and a data analysis module configured to determine patterns of the stance or movement based on the plurality of measurements. The determining patterns of the stance or movement can comprise: performing an automatic segmentation on the plurality of measurements; performing a metrics extraction on results of automatically segmentation; performing a dimension reduction on the plurality of metrics extracted; and/or performing a machine learning classification on the metrics being dimensionally reduced.

The performing of the machine learning classification can comprise: performing support vector machine (SVM) for data training; performing ensemble boosting for increasing classification performance.; performing leave-one-out standard for cross-validation (LOOCV) for inhibiting overfitting in classification; and/or performing ML based majority voting for reducing class-label noise in classification. The plurality of measurements can comprise measurements of force, pressure, kinetic, and/or temporal parameters of the stance or movements of the object.

In another embodiment, a method for assessing stance or mobility of an object standing or moving, can comprise: obtaining a plurality of measurements with respect to the stance or movements of the object; and determining patterns of the stance or movement based on the plurality of measurements by performing machine learning (ML) based classification. The plurality of measurements can comprise measurements of force, pressure, kinetic, and/or temporal parameters of the stance or movements of the object. The determining patterns of the stance or movement can comprise: automatically segmenting the plurality of measurements; extracting a plurality of metrics from the measurements segmented; and/or reducing dimensions of the plurality of metrics extracted for the ML based classification to perform on. The performing of the machine learning (ML) based classification can comprise performing support vector machine (SVM) for data training.

The method can further comprise: performing ensemble boosting for increasing classification performance; performing leave-one-out standard for cross-validation (LOOCV) for inhibiting overfitting in classification; and/or performing ML based majority voting for reducing class-label noise in classification.

In another embodiment, a (non-transitory) machine-readable medium (e.g., a (non-transitory) computer-readable medium) can comprise instructions stored thereon that, when executed by a processor, cause the processor to: obtain a plurality of measurements with respect to the stance or movements of the object; and determine patterns of the stance or movement based on the plurality of measurements by performing machine learning (ML) based classification. The plurality of measurements can comprise measurements of force, pressure, kinetic, and/or temporal parameters of the stance or movements of the object. The determining of the patterns of the stance or movement can comprise: automatically segmenting the plurality of measurements; extracting a plurality of metrics from the measurements segmented; and/or reducing dimensions of the plurality of metrics extracted for the ML based classification to perform on The performing of the machine learning (ML) based classification can comprise-performing support vector machine (SVM) for data training; performing ensemble boosting for increasing classification performance; performing leave-one-out standard for cross-validation (LOOCV) for inhibiting overfitting in classification; and/or performing ML based majority voting for reducing class-label noise in classification.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:
1. A cyber-physical system (CPS) pressure based sensing system for assessing stance or movements of an object standing or moving, the system comprising:
   a sensing and data acquisition device comprising at least one piezoresistive transducer; and
   a data analyzer in operable communication with the sensing and data acquisition device,
   the data analyzer further comprising a data analysis module configured to determine patterns of the stance or movement based on the plurality of measurements, and
   the determining of the patterns of the stance or movement comprising:
      performing an automatic segmentation on the plurality of measurements;
      performing a metrics extraction on results of the automatic segmentation;
      performing a dimension reduction on the plurality of metrics extracted; and
      performing a machine learning classification on the metrics being dimensionally reduced.
2. The CPS pressure based sensing system according to claim 1, the sensing and data acquisition device further comprising:
   a wireless communication module for wirelessly transmitting the measurements to the data analyzer; and
   a power management module.
3. The CPS pressure based sensing system according to claim 1, the at least one piezoresistive transducer being configured to obtain a plurality of measurements with respect to the stance or movements of the object.
4. The CPS pressure based sensing system according to claim 1, the data analyzer comprising a signal receiving module configured to wirelessly receive the measurements from the sensing and data acquisition device.

5. The CPS pressure based sensing system according to claim 1, the data analyzer further comprising a data storage module.

6. The CPS pressure based sensing system according to claim 1, the performing of the machine learning classification comprising performing support vector machine (SVM) for data training.

7. The CPS pressure based sensing system according to claim 6, the performing of the machine learning classification further comprising:
performing ensemble boosting for increasing classification performance;
performing leave-one-out standard for cross-validation (LOOCV) for inhibiting overfitting in classification; and
performing ML based majority voting for reducing class-label noise in classification.

8. The CPS pressure based sensing system according to claim 1, the plurality of measurements comprising measurements of at least one of force, pressure, kinetic, and temporal parameters of the stance or movements of the object.

9. The CPS pressure based sensing system according to claim 1, the plurality of measurements comprising measurements of force, pressure, kinetic, and temporal parameters of the stance or movements of the object.

10. A method for assessing stance or movements of an object standing or moving, the method comprising:
obtaining a plurality of measurements with respect to the stance or movements of the object; and
determining patterns of the stance or movement based on the plurality of measurements by performing machine learning (ML) based classification,
the determining of the patterns of the stance or movement comprising:
automatically segmenting the plurality of measurements;
extracting a plurality of metrics from the measurements segmented; and
reducing dimensions of the plurality of metrics extracted for the ML based classification to perform on.

11. The method according to claim 10, plurality of measurements comprising measurements of at least one of force, pressure, kinetic, and temporal parameters of the stance or movements of the object.

12. The method according to claim 10, the plurality of measurements comprising measurements of force, pressure, kinetic, and temporal parameters of the stance or movements of the object.

13. A method for assessing stance or movements of an object standing or moving, the method comprising:
obtaining a plurality of measurements with respect to the stance or movements of the object; and
determining patterns of the stance or movement based on the plurality of measurements by performing machine learning (ML) based classification,
the performing of the machine learning (ML) based classification comprising performing support vector machine (SVM) for data training.

14. The method according to claim 13, further comprising performing ensemble boosting for increasing classification performance.

15. The method according to claim 14, further comprising performing leave-one-out standard for cross-validation (LOOCV) for inhibiting overfitting in classification.

16. The method according to claim 15, further comprising performing ML based majority voting for reducing class-label noise in classification.

17. A cyber-physical system (CPS) pressure based sensing system for assessing stance or movements of an object standing or moving, the system comprising:
a sensing and data acquisition device comprising at least one piezoresistive transducer; and
a data analyzer in operable communication with the sensing and data acquisition device,
the sensing and data acquisition device further comprising:
a wireless communication module for wirelessly transmitting the measurements to the data analyzer; and
a power management module,
the at least one piezoresistive transducer being configured to obtain a plurality of measurements with respect to the stance or movements of the object,
the data analyzer comprising:
a signal receiving module configured to wirelessly receive the measurements from the sensing and data acquisition device;
a data storage module; and
a data analysis module configured to determine patterns of the stance or movement based on the plurality of measurements,
the determining of the patterns of the stance or movement comprising:
performing an automatic segmentation on the plurality of measurements;
performing a metrics extraction on results of the automatic segmentation;
performing a dimension reduction on the plurality of metrics extracted; and
performing a machine learning classification on the metrics being dimensionally reduced,
the performing of the machine learning classification comprising:
performing support vector machine (SVM) for data training;
performing ensemble boosting for increasing classification performance;
performing leave-one-out standard for cross-validation (LOOCV) for inhibiting overfitting in classification; and
performing ML based majority voting for reducing class-label noise in classification, and
the plurality of measurements comprising measurements of at least one of force, pressure, kinetic, and temporal parameters of the stance or movements of the object.

18. The method according to claim 13, the determining of the patterns of the stance or movement comprising:
automatically segmenting the plurality of measurements;
extracting a plurality of metrics from the measurements segmented; and
reducing dimensions of the plurality of metrics extracted for the ML based classification to perform on.

19. The method according to claim 10, performing of the machine learning (ML) based classification comprising performing support vector machine (SVM) for data training.

20. The method according to claim 19, further comprising:
performing ensemble boosting for increasing classification performance;
performing leave-one-out standard for cross-validation (LOOCV) for inhibiting overfitting in classification; and performing ML based majority voting for reducing class-label noise in classification.

\* \* \* \* \*